US00PP09680P

United States Patent [19]

Olesen et al.

[11] Patent Number: Plant 9,680

[45] Date of Patent: Nov. 5, 1996

[54] SHRUB ROSE PLANT NAMED 'POULDAVA'

[75] Inventors: Pernille Olesen; Mogens Olesen, both of Fredensborg, Denmark

[73] Assignee: DeVor Nurseries, Inc., Watsonville, Calif.

[21] Appl. No.: 414,532

[22] Filed: Mar. 31, 1995

[51] Int. Cl.[6] ..... A01H 5/00

[52] U.S. Cl. ..... Plt./1

[58] Field of Search ..... Plt./1, 22, 26

[56] References Cited

U.S. PATENT DOCUMENTS

P.P. 5,105 9/1983 Meilland ..... Plt./1

*Primary Examiner*—Howard J. Locker

*Attorney, Agent, or Firm*—Christie, Parker & Hale, LLP

[57] ABSTRACT

A shrub rose variety producing pink flowers.

1 Drawing Sheet

SUMMARY OF THE INVENTION

The present invention relates to a new and distinct shrub rose variety which was originated by our crossing as seed and pollen parents two unnamed and undistributed seedlings of our creation. The varietal denomination of this new rose is 'Pouldava'.

Among the novel characteristics possessed by this new variety which distinguish it from its parents and all other varieties of which we are aware are its attractive pink flowers borne on a bushy, vigorous plant.

Asexual reproduction by budding of the new variety as performed in Watsonville, Calif., shows that the foregoing and other distinguishing characteristics come true to form and are established and transmitted through succeeding propagations. Other known useful forms of asexual reproduction may be also employed.

BRIEF DESCRIPTION OF ILLUSTRATIONS

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

Parentage: Seedling.

*Seed parent.*—Unnamed, unpatented seedling.

*Pollen parent.*—Unnamed, unpatented seedling.

Class: Shrub.

The following is a detailed description of the new variety, from specimens grown outdoors in Watsonville, Calif., in the month of September. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

FLOWER

Blooming habit: Recurrent.

A. Bud:

(1) *Size.*—Small.

(2) *Form.*—Round to slightly ovoid.

(3) *Color.*—When sepals first divide, bud color is near 62D.

(4) *Sepals.*—About 1 cm to 2 cm long, spread and reflex when bloom opens; some sepals are foliaceous. Color: Near 138B.

(5) *Peduncle.*—Length: About 4½ cm to about 5 cm. Aspect: Numerous small prickles. Strength: Erect, sturdy. Color: Near 139C.

(6) *Bracts.*—One or two, near 132C fading to near 191C, elliptical with leaf-pointed ends about 4½ cm below calyx.

B. Bloom:

(1) *Size.*—Average size when fully expanded — about 5 cm to about 6 cm.

(2) *Borne.*—Sprays of about 3 to 17 blooms.

(3) *Form.*—Flower shape is generally round, outer petals quill to points, inner petals tend to curl or fold longitudinally resulting in informal flower form.

(4) *Petalage.*—Number of petals under normal conditions — about 55 to 65.

(5) *Color* (⅓ to ½ open).—Outer petals — Top surface near 55B to 55C where petals bunch to near 56A to 56D at outer petals; Undersurface: near 56D. Base of petals: Near 155C. General tonality from a distance: Pink.

(6) *Color (fully open).*—Outer petals — Top surface: between near 56A to 56D; Undersurface: between near 56C and 56D. Inner petals — Top surface: between near 56C and 56D; Undersurface: near 56D. Base of petals: Near 155C. General tonality from a distance: Pink.

(7) *Color change.— Lightens slightly. Petal top surface: Between near* 56C and 56D. Petal undersurface: Near 56D. General tonality at a distance: Pink.

C. Petals:

(1) *Texture.*—Smooth.

(2) *Appearance.*—Matte (3) *Form.*—Elliptic.

(4) *Arrangement.*—Imbricated at first, becoming ruffled.

(5) *Petaloids.*—Many.

(6) *Fragrance.*—None.

(7) *Lasting quality.*—Not a cut flower variety but several days on plant.

(8) *Persistence.*—Petals drop off cleanly.

REPRODUCTIVE ORGANS

A. Stamens:

(1) *Arrangement.*—Irregularly arranged around styles.

(2) *Stamens.*—Near 22A.

(3) *Anthers.*—Color near 22A.
(4) *Filaments.*—Near 14C.
(5) *Pollen.*—Color near 22A.

B. Pistils:
(1) *Styles.*—Bunched, uneven length.
(2) *Stigmas.*—Color near 160A.

C. Characteristics of hips: Not observed.

PLANT

A. *Form.*—Mounds.

B. *Growth.*—Very vigorous; about 53 cm to about 61 cm in height and width at first season.

C. Foliage: Compound 3, 5 or 7 leaflets.
(1) *Size.*—Medium.
(2) *Quantity.*—Abundant.
(3) *Color.*—New foliage — upper side near 146A; underside near 146B; mature foliage — upper side near 137A; underside near 138A.
(4) *Shape.*—Pinnate.
(5) *Texture.*—Upper side smooth and dull; underside with visible veins.
(6) *Edge.*—Serrate.
(7) *Serration.*—Denticulate.
(8) *Leaf stem.*—Color — medium green.
(9) *Stipules.*—Adnate, bearded, parallel, with glands on top.
(10) *Rachis.*—Small prickles or hairs.
(11) *Petioles.*—Top near 146B, underside near 146C.
(12) *Auricle.*—Distinctive slender extensions.
(13) *Resistance to disease.*—Very resistant to black-spot, mildew and rust.

D. Wood:
(1) *New wood.*—Color near 146C, bark smooth.
(2) *Old wood.*—Color near 146B, bark smooth.

E. Thorns:
*Quantity.*—On main stalk, some laterals from stalk, few.
*Form.*—Curved downward.
*Length.*—Medium.
*Color.*—Near 161B.
*Position.*—Irregular.
*Prickles.*—None.

G. Winter hardiness: Winter hardy in Denmark and in Watsonville, Calif.

I claim:

1. A new and distinct shrub rose plant variety, substantially as shown and described.

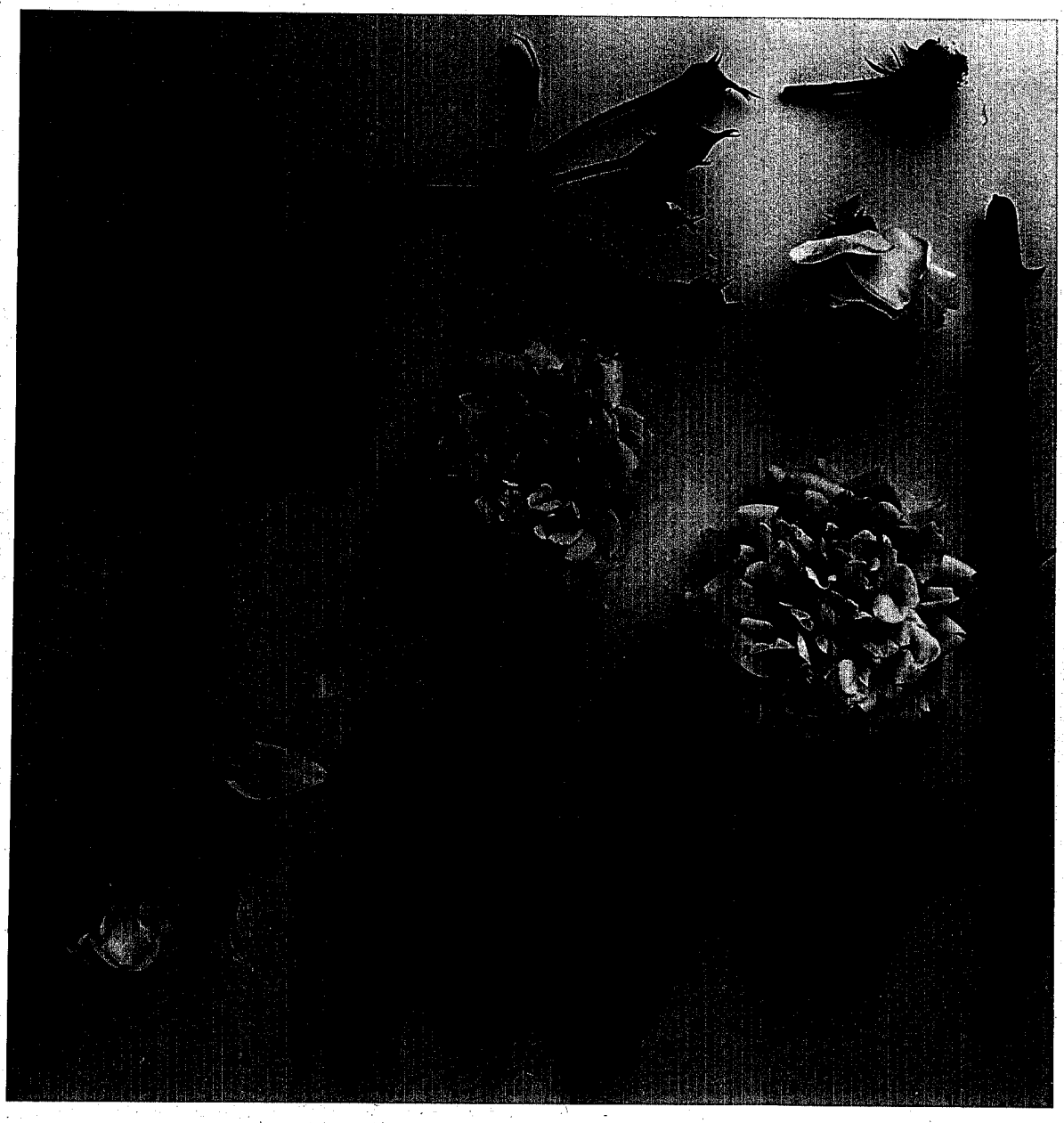

* * * * *